(12) United States Patent
Welsh et al.

(10) Patent No.: US 6,823,749 B1
(45) Date of Patent: Nov. 30, 2004

(54) SEDIMENT SAMPLER FOR AQUATIC ENVIRONS

(75) Inventors: Stuart A. Welsh, Morgantown, WV (US); Lara B. Hedrick, Morgantown, WV (US); James D. Hedrick, Morgantown, WV (US)

(73) Assignee: The United States of America as represented by the Secretary of the Department of the Interior, Washington, DC (US)

( * ) Notice: Subject to any disclaimer, the term of this patent is extended or adjusted under 35 U.S.C. 154(b) by 0 days.

(21) Appl. No.: 10/609,864

(22) Filed: Jul. 1, 2003

(51) Int. Cl.⁷ ............................ G01N 15/06; G01N 1/12

(52) U.S. Cl. ................ 73/864.64; 73/863.22; 73/61.71

(58) Field of Search ................... 73/864.64, 863.22, 73/864, 61.71

(56) References Cited

U.S. PATENT DOCUMENTS

| | | | |
|---|---|---|---|
| 3,534,605 A | 10/1970 | De Koning et al. | 73/290 |
| 3,715,913 A | 2/1973 | Anderson | 73/61 R |
| 4,026,151 A | 5/1977 | Fitzgerald | 73/194 R |
| 2002/0043117 A1 * | 4/2002 | Dostie | 73/864.64 |

OTHER PUBLICATIONS

Berkman, H.E. and C.F. Rabeni, 1987. Effects of siltation on stream fish communities. Environ. Biol of Fishes. 18:285–294.

Platts, W.S., R.J. Torquemada, M.L. McHenry, and C.D. Graham. 1989. Changes in salmon spawning and rearing habitat from in released delivery of fine sediment to the South Fork Salmon River, Idaho. Trans. Am. Fish. Soc. 118:274–283.

Clarke, K.D. and D.A. Scruton. 1997. Use of Wesche method to evaluate fine–sediment dynamics in a small boreal forest headwater streams. North American Journal of Fish Management 17–188–193.

Garrett, J.W. and D.H. Bennett. 1996. Evaluation of fine sediment intrusion into Whitlock–Vibert boxes. North American Journal of Fisheries Management 16:448–452.

Wesche, T.A., D.W. Reiser, V.R. Hasfurther, W.A. Hubert, and Q.D. Skinner. 1989. New technique for measuring fine sediment in streams. North American Journal of Fisheries Management 9:234–238.

* cited by examiner

*Primary Examiner*—Hezron Williams
*Assistant Examiner*—Tamiko Bellamy
(74) *Attorney, Agent, or Firm*—Mark Homer

(57) ABSTRACT

A sediment measuring device has a base that is fixed into the bottom of a body of water. A removable trap, having a retaining matrix, inserts into the fixed base to capture and retain moving sediment within the trap over a given period of time. The trap is removed from the base, and may be replaced with a second trap, after which the trapped sediment is measured.

12 Claims, 1 Drawing Sheet

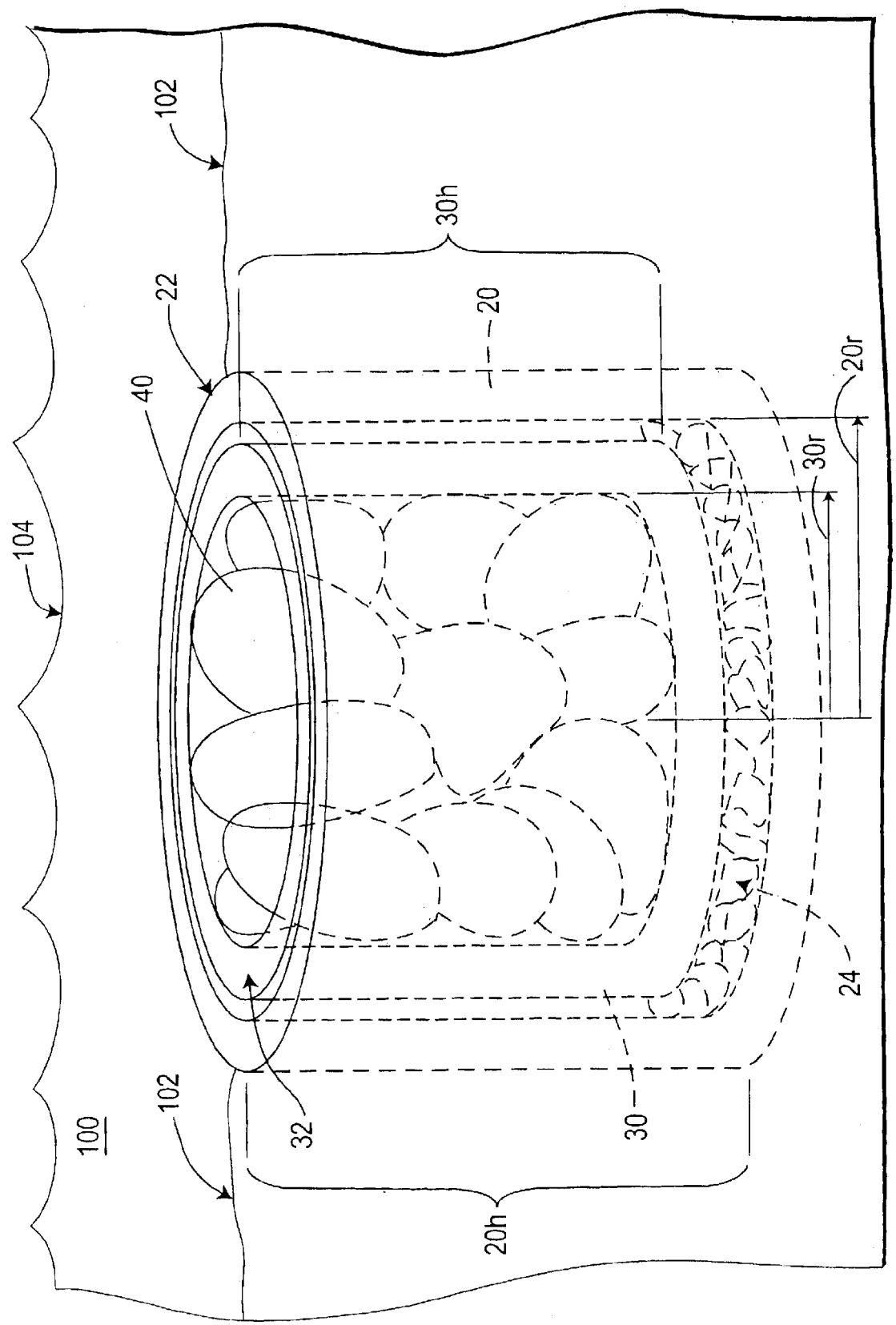

SEDIMENT SAMPLER FOR AQUATIC ENVIRONS

The invention described herein may be manufactured and used by or for the government of the United States of America for governmental purposes without the payment of any royalties thereon or therefor.

BACKGROUND OF THE INVENTION

1. Field of the Invention

The present invention provides a device, method using the device, for sampling sediment accumulation in a body of water.

2. Brief Description of the Related Art

Lacking in many field of inquiry, including aquatic biology, aquatic ecology, invertebrate zoology, environmental engineering, forestry and geological sciences, is the ability to accurately quantify sedimentation in aquatic systems. Quantification of the sedimentation is necessary for assessing environmental impact of regulations and adequate scientific knowledge of aquatic ecosystems. In aquatic ecology and invertebrate zoology measurement of sedimentation relates to aquatic organisms, whereas environmental engineering and forestry measurement of sedimentation relate to construction and logging, respectively. In geological science, sedimentation analysis is necessary for proper understandings of the relationship among sedimentation, stream fluvial mechanics, and bed load movements.

Core sampling is the most common method of quantifying sedimentation in streams and assessing affects of sedimentation of aquatic communities. However, core sampling is labor and equipment intensive, and disturbs a portion of the stream bed during each use. Additionally, core sampling is generally used for single or annual measurements of sediment, but is ineffective for repeat sampling over a long time interval. Another device, the Whitlock-Vibert box, disturbs stream beds when samples are obtained or a new sampler is placed in the stream.

There is a need in the art to provide an accurate sedimentation quantification system. The present invention addresses this and other needs.

SUMMARY OF THE INVENTION

The present invention includes a sediment measuring device for aquatic environs comprising a base having a planar rim thereon, a trap insertable into the base wherein the rim of the trap remains substantially flush with the planar rim of the base and a retaining matrix insertable within the trap effective for retaining sediment within the trap.

The present invention also includes a process for measuring sediment with a sediment measure device, comprising the steps of providing a sediment measuring device having a base with a planar rim thereon, a trap inserted into the base with the rim of the trap substantially flush with the planar rim of the base and a retaining matrix inserted within the trap effective for retaining sediment within the trap, locating the sediment measuring device in a body of water for a period of time, removing the trap with the retaining matrix retaining sediment within the trap and measuring the sediment within the removed trap. The present invention additionally includes a measured sediment product produced by this process.

BRIEF DESCRIPTION OF THE DRAWINGS

FIG. 1 illustrates a sediment measuring device of the present invention, having a base and trap inserted into the base, with a retaining matrix in the trap placed in the bottom of a water body.

DETAILED DESCRIPTION OF THE PREFERRED EMBODIMENT

The present invention provides a sediment measuring device, also referred to as a sediment sampler, for aquatic environs, particularly to quantify sedimentation in small streams. As detailed below, the sediment measuring device of the present invention includes a base having an insertable trap which is filled with a retaining matrix.

As seen in FIG. 1, the sediment measuring device 10 of the present invention includes a base 20. The base 20 may be any geometric shape having a planar rim 22 on the top of the base 20, with a preferred configuration including a cylindrical shape. The base 20 includes appropriate dimensions for containment and holding the trap 30, described below, and is placed in the bottom 102 of a subject water body 100, such as a stream bed 102, to be sampled. For reference in FIG. 1, the surface 104 of the water body 100 is shown. Generally, the base 20 replicates the geometric configuration of the trap 30 in a larger size for the trap 30 to conveniently fit securely within the base 20. As height and circumference dimensions of the base 20 increase, difficulty increases in placing the base 20 into the stream bed 102 from the increased amount of sand, mud or other material that is removed from the bottom 102 of the subject water body 100 to insert the base 20.

The base 20 and trap 30 may comprises similar or different compositions that remain effective in an aquatic environment over extended periods of time. Representative compositions include metals such as steel, copper, and the like, concrete, plastics such as thermoplastic and other polymeric composition including polyvinylchloride, polyethylene, polypropylene, and combinations and composites these and other materials suitable for measurement of sediment as taught herein. Preferably, both the base 20 and trap 30 comprise polyvinylchloride.

As further seen in FIG. 1, the trap 30 of the sediment measuring device 10 has a similar cup shape as the base 20 and is readily removable from the base 20 after being inserted therein. Additionally the trap 30 holds the retaining matrix 40. When the trap 30 is inserted within the base 20, the rim 32 of the trap 30 remains substantially flush with the planar rim 22 of the base 20 that effectively eliminates any barrier to the collection of sedimentation in the sediment measuring device 10 as the rims 22, 32 remain level with the stream bed 102. A lip is preferably used on the inside of the base 20 to level the trap rim 32 with the base rim 22. Fill 24 may be used in interior of the base 20 to stabilize the base 20 on the stream bed 102, or when the lip is absent, level the trap rim 32 with the base rim 22.

The trap 30 may include any appropriate dimensions for collection of sedimentation, as taught herein, with preferred dimensions including, for example without limitation, trap 30 heights (30$h$) of from about 1 inch to about 6 inches, more preferably from about 1.5 inches to about 4 inches, and most preferably from about 2 inches to about 3 inches. Preferably, the rim 32 of the trap 30 has a substantially circular diameter with a radius (30$r$) ranging from about 2 inches to about 8 inches, with a more preferred radius (30$r$) of the rim 32 of the trap 30 ranging from about 3 inches to about 5 inches.

Placed within the trap 30, the retaining matrix 40 is used to retain sediment once that sediment has entered the trap 30. As such, the retaining matrix 40 of the sediment measuring device 10 effectively impedes the exit of sediment that has entered the trap 30, trapping the sediment in the trap 30. The retaining matrix 40 may include singular or multi-part structures placed within the trap 30. Singular structures may include arrays, interconnected elements, embedded masses and other like structures that do not block sediment from entering the trap 30. Multi-part structure may include sectionalized masses, chunks, blocks, stars and other spatial geometric configurations, that are readily distinguishable from any collected sediment within the trap 30 while being resilient to degradation in an aquatic environment. Representative compositions of the retaining matrix include, for example without limitation, plastics, gravel, metal, glass, including composites and combinations thereof. Preferably the retaining matrix 40 comprises gravel or other gravel like materials. When in the form of a multi-part structure, the retaining matrix 40, e.g., gravel, preferably ranges in diameter from about 0.5 inches to about 1.5 inches, with a more preferred diameter range from about 0.5 inches to about 1.0 inches.

In one preferred embodiment, the above described sediment measuring device 10 includes a plastic base 20 having a height (20*h*) of about 4 inches and a planar rim 22 having a diameter with a radius (20*r*) of about 5 inches, with the trap 30 having a height (30*h*) of about 2 inches and a planar rim 32 having a diameter with a radius (30*r*) of about 4.75 inches inserted into the base 20 in a manner permitting the rim 32 of the trap 30 to remain substantially flush with the planar rim 22 of the base 20. Within the trap 30, the retaining matrix 40 has a gravel composition with a mean diameter of about 0.75 inches.

As further seen in FIG. 1, in operation sediment measurement occurs by locating the sediment measure device 10 of the present invention into the bottom 102 of a body of water 100 over a period of time. Typically, a cavity is dug within the bottom 102 of the water body 100 of sufficient dimensions to allow insertion of the base 20 that leaves the rim 22 portion of the base 20 level with the bottom of the water body 100 within this hole. After insertion of the base 20 into the hole, the remainder of the hole is filled to provide a continuous level of the water body bottom 102 to the edge of the base rim 22. The trap 30 and retaining matrix 40, is preferably placed within the base 20 after insertion in the hole to minimize any influx of sediment into the trap 30 while the sediment measuring device 10 is being placed into the stream bed 102. Alternatively, the trap 30 may remain within the base 20 during placement of the base 22 into the stream bed 102, with the trap 30 preferably extracted from the base 20, after placement, and cleaned of any sediment that has entered the trap 30 due to the placement process. Cleaning generally includes rinsing with water from the water body 100, and dumping the rinsed product, downstream from the located base 20. The rim 32 of the trap 30 remains level with the rim 22 of the base 20 once the trap 30 is placed into the base 20. With the placement of the sediment measuring device 10 in the body of water 100, i.e., the combination of the base 20, trap 30 and retaining matrix 40, the sediment measuring device 10 is left undisturbed for a period of time that is preferably set prior to removing the trap 30 from the base 20 or measured at the time of trap 30 removal.

The period of time that sediment is accumulated in the trap 30 may include any appropriate time for investigatory analysis, which may include a couple of hours, days, weeks, months, etc. Representative time periods preferably range from about four months or less, more preferably from about one week to about five months, still more preferably from about one week to about three months, and most preferably from about one week to about five weeks. At the specified elapsed time period, the trap 30, with the retaining matrix 40 therein, is removed in a manner to retain to accumulated sediment in the trap 30, and the sediment is measured. Preferably, a second trap 30 is inserted into the open base 20 immediately after trap 30 removal to continue additional measurement of sediment. Alternatively a blocking mass, such as an inverted trap 30, may be inserted into the base 20 to keep the base 20 from filling up with sediment while the removed trap 30, containing the sediment sample, is taken for analysis. Measurement of the sediment may include any amounts or characteristics of interest including, for example without limitation, the weight of the sediment, composition of parts or all of the sediment, the amount or volume of sediment collected, and other quantifying or qualifying aspects of sediment inquiry. Preferably, the trap 30 is taken to a laboratory, such as an on-site mobile lab or remote permanent lab, to analyze the sediment.

The present invention is preferably used to estimate sedimentation during a short time period in moderately flowing waters or to monitor changes in sedimentation in calmer waters over a longer time period. Most preferably, the sediment measuring device 10 measures sedimentation as a comparative event, such as comparing sedimentation at a given geographical point before and after a disturbance, including for example an upstream construction site, a local dam, waste water dumping, dredging operations, and other such predictable events. Time periods of analysis may include, for example, monthly sampling over a five year period, weekly sampling over a two year period, on-going quarterly sampling of indefinite length, etc. Preferably, with the removal of the trap 30 from the base 20, a second trap 30 is inserted into the base 20 for continuous sampling at a given base 20 site.

Measurement of the sediment preferably includes removal of the retaining matrix 40 from the trap 30, after which the sediment is dried such as with a heating step of the sediment sample. Length of drying times varies with the sample, such as type and composition, and the amount of water within the sample, with the length of time being determinable by one skilled in the art. Once the sample has settled, water is drained off and the sample is placed in an oven. Drying should occur at a temperature and time period effective for drying the sediment to a constant weight. Lower drying temperatures are preferred to preserve the integrity of the sediment for qualitative analysis, when desired. Representative drying temperatures range from about 100EC or less, with preferred drying temperatures of from about 90EC or less, and increasing preferred drying temperatures ranges of from about 70EC to about 90EC, from about 70EC to about 80EC and from about 75EC to about 78EC. Representative drying times include, for example without limitation, period of times within the period of from about one day to about two weeks, such as from about one day to about four days, or from about 36 hours to about 48 hours.

Once dried, sediment may be sized to determine a particular size of interest. Sizing preferably includes the use of one or more sizing sieves where the dried sediment is sieved through increasing smaller sized sieves to characterize the size of component parts of the sediment. For example, dried sediment is originally sieved through a 10 mesh sieve, followed by a 40 mesh sieve, followed by sieving through a 100 mesh sieve. Other representative sieve sizes include size 4 (0.187 inches or 4.7 mm), size 8 (0.090 inches or 2.28 mm), size 14 (0.055 inches or 1.4 mm) and size 20 (0.0386 or 0.98 mm). Additionally, specific chemical compounds or classes of compounds may be removed from the sediment and chemically analyzed, for example, extraction of arsenic with appropriate traps and analyzed with appropriate identifying methods.

Suitable aquatic environs for practicing the sediment measuring device 10 of the present invention preferably include, for example without limitation, moving or flowing bodies of water 100 such as lakes, streams, rivers, ditches, estuaries, marshes, bayous and combinations of these water bodies. Preferably, the sediment measuring device 100 is used in non-turbulent waters.

The measured sediment product obtained by the present invention enables researchers to track, monitor, quantify, classify, or otherwise analyze sedimentation within a water body 100. This allows corrective actions to be taken, when needed, for such purposes as pollution abatement, dredging operations, forestry management, zoning, marine animal studies, and the like.

A marker may be placed in the area, either on shore or in the water body 100, in a manner that does not impede proper sediment measurement from the sediment measuring device 10 such as, for example without limitation, placing a tagged poll downstream and positioned in an effectively non-interfering distance from the sediment measuring device 10. Distances may include 10 inches, 2 feet, 5 feet, or other such distances that are determinable by those skilled in the art taking into account water turbulence, cross-currents, sources and flows of sediment, water level changes, flows and sources of water entering and leaving the water body 100, rain accumulation patterns, navigational routes, and other such factors determinable by those skilled in the art.

For a given analysis and/or body of water 100, the sediment measuring device 10 may be appropriately configured or modified such as, for example without limitation, fixing a screen over the top of the trap 30, using a given type of retaining matrix 40, using elongated trap 30 configurations for given underwater terrains, using multiple traps within a given base 20, having a releasable locking or attaching mechanism between the base 20 and trap 30, etc. Increases of the turbulence of the subject water body 100 or sampling times may necessitate the use of an anchoring component of the base 20, such as added weight which may include a metal base, projections or fanned parts of the base 20 for holding within the bottom of the subject water body 100, and other like mechanisms to moor the base 20 at a fixed point in the subject water body 100.

EXAMPLE 1

A sediment sampler was constructed having a base made from 4 inch schedule 40 PVC union with a height of 9.53 cm (3.75 inches). A grinding stone was used to sand down the inner edge of the upper portion of the base of the 4 inch PVC union to a depth equal to the height of the trap that allowed the trap to move freely in and out of the base with a lip created that supported the inserted trap. The trap was constructed by fitting with silicon a 4 inch insert cap onto a 5 cm (deep) piece of 4 inch schedule 40 PVC pipe. The trap was filled with gravel having a 0.5 inch diameter or greater. The base was embedded into the stream bed to a depth where the base top was flush with the bottom of the stream. With the top of the base flush with the bottom of the stream, gravel from the stream bed was used to fill the base up to the level where the trap would rest to stabilize the base. Once the base was embedded, the trap, and gravel, was inserted into the base. This created a substantially circular opening level with the stream bed of the trap encircled by the base with minimal spacing between the trap and base that, at the appropriate time, facilitated easy insertion and removal of the base. After a period of one week, the trap was removed and replaced with a second trap in the base that remained embedded in the stream bed.

The sediment sampler in the times over a long stream, or other water body, may be retrieved multiple times over a long sampling duration. The unique design of the base embedded into the stream bottom and trap which inserts into the base and is removable allows for minimal disturbance of the stream substrate after first deployment and prevents loss of sediment upon retrieval of the sediment sample.

The foregoing summary, description, and examples of the present invention are not intended to be limiting, but are only exemplary of the inventive features which are defined in the claims.

What is claimed is:

1. A sediment measuring device for aquatic environs, comprising:
    a base having an opening with a planar rim thereon;
    a trap insertable into the opening, having a trap opening with a rim base wherein the rim of the trap remains substantially flush with the planar rim of the base; and,
    a retaining matrix insertable within the trap effective for retaining sediment within the trap.

2. The sediment measuring device of claim 1, wherein the height of the trap ranges from about 2 inches to about 6 inches.

3. The sediment measuring device of claim 1, wherein the height of the trap ranges from about 3 inches to about 6 inches.

4. The sediment measuring device of claim 1, wherein the base and trap independently comprise a composition, selected from the group consisting of steel, concrete, polyvinylchloride, polyethylene, polypropylene, and combinations and composites thereof.

5. The sediment measuring device of claim 4, wherein the base and trap independently comprise polyvinylchloride.

6. The sediment measuring device of claim 1, wherein the rim of the trap has a substantially circular diameter with a radius ranging from about 3 inches to about 10 inches.

7. The sediment measuring device of claim 1, wherein the rim of the trap has a substantially circular diameter with a radius ranging from about 5 inches to about 8 inches.

8. The sediment measuring device of claim 1, wherein the retaining matrix comprises a composition selected from the group consisting of plastic, gravel, metal, glass, and combinations thereof.

9. The sediment measuring device of claim 8, wherein the retaining matrix comprises gravel.

10. The sediment measuring device of claim 8, wherein the size of the gravel ranges in diameter from about 0.5 inches to about 1.5 inches.

11. The sediment measuring device of claim 8, wherein the size of the gravel ranges in diameter from about 0.5 inches to about 1.0 inches.

12. A sediment measuring device for aquatic environs, comprising:
    a plastic base having a height of from about 2 inches to about 6 inches and a planar rim having a substantially circular opening with a diameter with a radius of from about 3 inches to about 10 inches;
    a trap inserted into the base wherein the rim of the trap remains substantially flush with the planar rim of the base; and,
    a retaining matrix gravel composition inserted within the trap having a mean diameter of from about 0.5 inches to about 1.0 inches.

* * * * *